United States Patent [19]
Narciso, Jr.

[11] Patent Number: 5,700,243
[45] Date of Patent: Dec. 23, 1997

[54] BALLOON PERFUSION CATHETER

[75] Inventor: Hugh L. Narciso, Jr., Santa Barbara, Calif.

[73] Assignee: PDT Systems, Inc., Santa Barbara, Calif.

[21] Appl. No.: 653,461

[22] Filed: May 24, 1996

Related U.S. Application Data

[63] Continuation of Ser. No. 378,392, Jan. 26, 1995, abandoned, which is a continuation of Ser. No. 145,292, Oct. 29, 1993, abandoned, which is a continuation of Ser. No. 969,106, Oct. 30, 1992, abandoned.

[51] Int. Cl.$^6$ ................................................ A61M 29/00
[52] U.S. Cl. ........................ 604/102; 604/20; 604/53; 606/7; 606/15; 606/16; 606/194; 607/88
[58] Field of Search ........................ 604/96–97, 102, 604/43, 50, 52, 53, 113, 114, 19–21; 606/191–194, 2, 7, 10–16; 600/101, 104, 108, 116, 153, 156, 178, 181, 182, 184, 185; 607/88, 89, 92, 96; 128/898

[56] References Cited

U.S. PATENT DOCUMENTS

| | | | |
|---|---|---|---|
| 4,445,892 | 5/1984 | Hussein et al. | 606/15 |
| 4,857,054 | 8/1989 | Helfer | 604/102 |
| 4,944,745 | 7/1990 | Sogard et al. | 604/103 |
| 5,006,119 | 4/1991 | Acker et al. | 604/96 |
| 5,019,075 | 5/1991 | Spears et al. | 606/15 |
| 5,116,317 | 5/1992 | Carson, Jr. et al. | 604/96 |
| 5,117,831 | 6/1992 | Jang et al. | 604/96 |
| 5,137,513 | 8/1992 | McInnes et al. | 604/96 |
| 5,156,594 | 10/1992 | Keith | 604/96 |
| 5,169,395 | 12/1992 | Narciso, Jr. | 606/7 |
| 5,188,592 | 2/1993 | Hakki | 604/96 |
| 5,201,317 | 4/1993 | Kanazawa et al. | 606/15 |
| 5,246,437 | 9/1993 | Abela | 606/15 |

*Primary Examiner*—Michael Powell Buiz
*Assistant Examiner*—Ronald K. Straight, Jr.
*Attorney, Agent, or Firm*—Michael G. Petit

[57] ABSTRACT

The present invention is an improved balloon-type catheter with an integral fiber optic assembly for delivering light to a intraluminal target wherein the improvement comprises the use of a perfusion channel to bypass the balloon near the tip of the catheter. The bypass channel enables a fluid material such as oxygen or blood to flow around the inflated balloon during photo-irradiation. A preferred embodiment of the balloon-type perfusion includes a body portion comprising an elongated, flexible, tubular sheath having proximal and distal ends. The body portion is internally partitioned into three longitudinal lumens. The first lumen contains the illuminating fiber optics that include a cylindrical light diffuser tip. The second lumen is an inflation passage for conducting inflation fluid to a balloon which coaxially surrounds the sheath overlying the diffuser tip terminus of the fiber optics near the distal end of the catheter. The third lumen, usually larger in cross-sectional area than the other two, serves as both a portion of a perfusion channel and as a conduit for a guidewire or other ancillary device. A portion of the perfusion channel exits the body portion proximal to the balloon providing fluid communication between the external surface of the sheath and the third lumen. The perfusion channel enables a fluid to flow from the proximal side of the inflated balloon to the distal side of the balloon while the balloon is inflated.

2 Claims, 3 Drawing Sheets

BALLOON PERFUSION CATHETER

CROSS REFERENCE TO RELATED APPLICATIONS

This is a continuation of application Ser. No. 08/378,392, filed Jan. 26, 1995, now abandoned, which is a continuation of Ser. No. 08/145,292, filed Oct. 29, 1993, now abandoned, which is a continuation of Ser. No. 07/969,106, filed Oct. 30, 1992, now abandoned.

BACKGROUND OF THE INVENTION

1. Field of the Invention

This invention relates generally to the field of interventional medical catheters, and more particularly, it relates to catheters used for intraluminal photodynamic therapy of atherosclerosis, cancer and similar medical procedures such as hyperthermia.

2. Prior Art

Photodynamic Therapy (PDT) has been shown to be a very effective method for treating tumors. PDT has also been proposed for treatment of cardiovascular disease, particularly atherosclerosis. PDT employs photosensitive target-selective molecules which are injected into the blood and selectively concentrated at a particular treatment site where they may be photoactivated to initiate target cell destruction. Conduction of light from a source such as a laser to the treatment site is accomplished through the use of a single or multiple fiber optic delivery system with special diffuser treatment tips. As the field of PDT matures, new light delivery systems are needed to treat specific sites. One such need is the ability to treat a luminal surface as, for example, to induce hyperthermia or perform PDT, or perform both simultaneously, while maintaining the flow of blood, oxygen or other sustaining fluids distal to the treatment site.

Treating cancer of the throat or any organ in the respiratory system poses unique problems. Treating this luminal surface with a device which is smaller than the lumen itself creates a dosimetry problem. If the delivery device is not in the center of the lumen, the treatment will be uneven. In addition, the lumen being treated will rarely be perfectly round. Any folds or irregularities in the luminal surface will create areas of shadowing. Inflatable balloons surrounding the treatment diffuser tip have been employed, however, any balloon which dilates the lumen will also serve to restrict the flow of oxygen through the lumen and asphyxiate the patient.

Dilation of a blood vessel such as an artery with a balloon catheter to perform photodynamic therapy will occlude the flow of blood distal to the catheter, causing ischemia. To prevent this, practitioners have proposed employing the strategy of repetitive inflation, treatment and deflation of the balloon in order to prevent ischemia and yet deliver a measurable and quantitative amount of light to the treatment site. Inflations, followed by repetitive deflations and reinflations, while preventing ischemia, are cumbersome and time consuming procedures. It is clear that a light transmitting catheter fitted with a diffusing tip having the ability to take a gas or fluid proximal to the balloon and deliver the fluid distal to the catheter tip without interrupting the delivery of light is desirable.

Delivery systems useful for PDT or hyperthermia are quite common. Some examples include a single fiber cylindrical diffuser, a spherical diffuser, a microlensing system, an over-the-wire cylindrical diffusing multi-fiber optic catheter, etc. Perfusion balloons have been used in the treatment of cardiovascular disease. The purpose of the prior art balloon perfusion catheter is as an emergency conduit to by-pass a collapsing stenosis or clogged vessel. If an interventional procedure causes a vessel to abruptly close down, a perfusion catheter is used to maintain the flow of blood to the distal vessel. One such catheter is the Advanced Cardiovascular System's Stack™ perfusion balloon catheter. The purpose of this catheter is to maintain patency of a collapsing vessel until the vessel can maintain itself or until a corrective procedure can be performed. Such catheters are inoperable for performing both perfusion and PDT.

SUMMARY OF THE INVENTION

Broadly, the present invention is a balloon-type photodynamic angioplasty catheter with an integral fiber optic assembly wherein the improvement comprises the use of a perfusion channel to bypass the balloon near the tip of the catheter. The bypass channel enables a fluid material such as oxygen or blood to flow around the balloon during photoirradiation of an interluminal surface. This improvement in prior art photodynamic angioplasty catheters and hyperthermia catheters permits the administration of photodynamic therapy or hyperthermia to the treatment site without the necessity for repeatedly inflating and deflating the balloon during treatment.

More specifically, a balloon type photodynamic angioplasty catheter in accordance with the present invention, includes an elongated, flexible, tubular sheath internally partitioned into three longitudinal lumens. The first lumen contains the illuminating fiber optics that include the diffuser tip. The second lumen is an inflation passage for conducting inflation fluid to the balloon that coaxially surrounds the sheath overlying the diffuser tip terminus of the fiber optics near the end of the catheter. The third lumen, usually larger in cross-section area than the other two, serves principally as a conduit for a guidewire or other ancillary device. The novel aspect of the photodynamic angioplasty catheter is a perfusion channel through the sheath which effectively bypasses the balloon portion of the catheter to enable a fluid to flow from the proximal side of the inflated balloon to the distal side of the balloon when the balloon is inflated. The perfusion channel comprises fenestrations in the catheter proximal to the balloon which provide fluid communication with the guidewire lumen.

It is an object of this invention to provide a balloon-type, medical catheter for photodynamic therapy which does not require repeated inflation and deflation to prevent ischemia or asphyxia during treatment.

A further object of the invention is to provide a balloon-type photodynamic therapy catheter which has improved dosimetry characteristics with respect to similar catheters requiring repeated inflation and deflation.

These and other aspects of the invention will become more apparent as we turn now to the description of the embodiment.

DESCRIPTION OF THE PREFERRED EMBODIMENT

Figure 1:
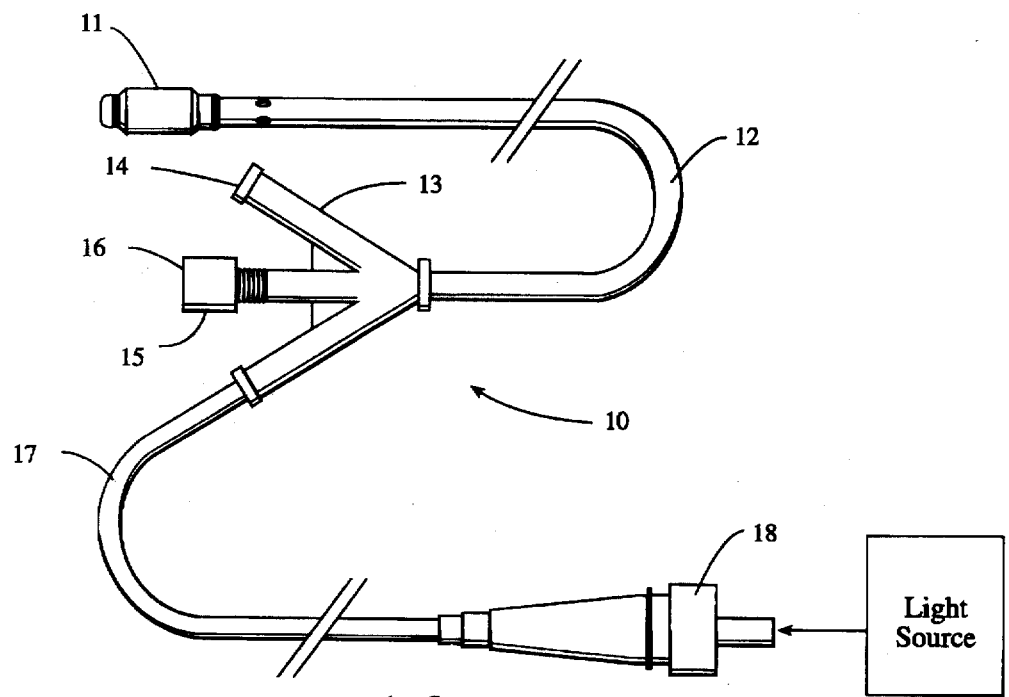
FIG. 1 is a plan view of a perfusion balloon catheter of the present invention suitable for photodynamic therapy.

Referring to the drawings, a balloon-type photodynamic angioplasty catheter 10 in accordance with the preferred embodiment of the present invention is described in detail. The catheter 10, as shown in FIG. 1, includes an elongate, flexible catheter body 12, formed from a single length of a suitable bio-compatible polymer. The catheter 10 is fitted with a balloon tip 11 and a 3-arm adapter 13. A fiber optic bundle 17 conducts light from a light source (not shown) but which is normally attached at optical connector 18 to the catheter 12. The 3-arm adapter has ports for balloon inflation/deflation 14, conveyance of the annular or cylindrical array of fibers into a bundle 17 and guidewire lumen 16 fitted with a hemostasis valve 15.

Figure 2:
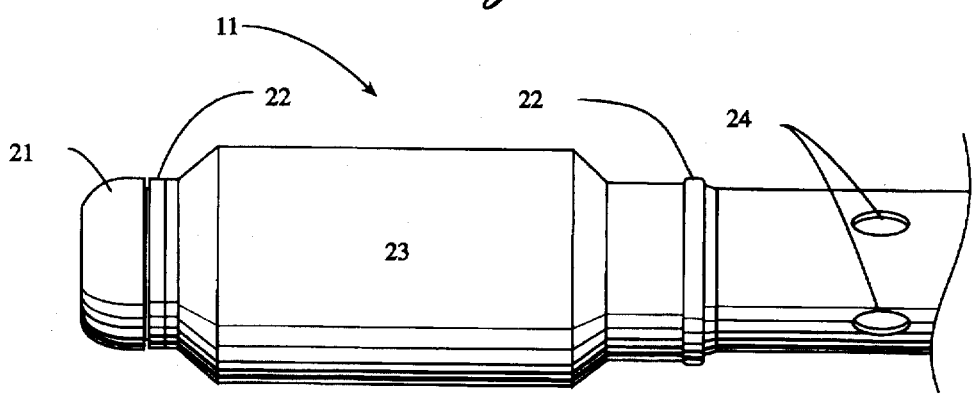
FIG. 2 is a perspective view of the distal tip of FIG. 1.

Turning now to FIG. 2 we see a close-up view of catheter tip 11. The catheter has a distal beveled tip 21 which enables the atraumatic introduction of the catheter within a vessel or lumen. The distal tip also has circumferential radiopaque bands 22 which serve to crimp the balloon 23 in place and to act as markers under fluoroscopic x-ray visualization. Proximal to the balloon 23 are three (only two are shown) perfusion ports 24 which allow the fluid (not shown) surrounding the catheter 11 to enter the body 12 of the catheter.

Figure 3:
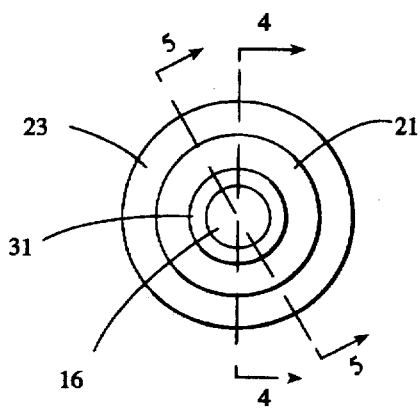
FIG. 3 is an end-on view of the catheter tip of FIG. 2.

As shown in FIG. 3, the guidewire lumen 16 is normally located in the center of the catheter body. A cone-shaped introducer portion 31 is employed to facilitate the introduction of a guidewire (not shown) into the lumen of the catheter. The beveled tip 21 of the catheter 11 further enables the atraumatic introduction of the distal tip into a tubular tissue under treatment. The balloon 23 is attached near the distal end of the catheter 12 so as to surround its exterior surface coaxially. The balloon 23 is normally made of a polymeric material such as polyethylene that provides high strength upon inflation. Such balloons are well known in the art and need not be described in further detail herein.

Figure 4:
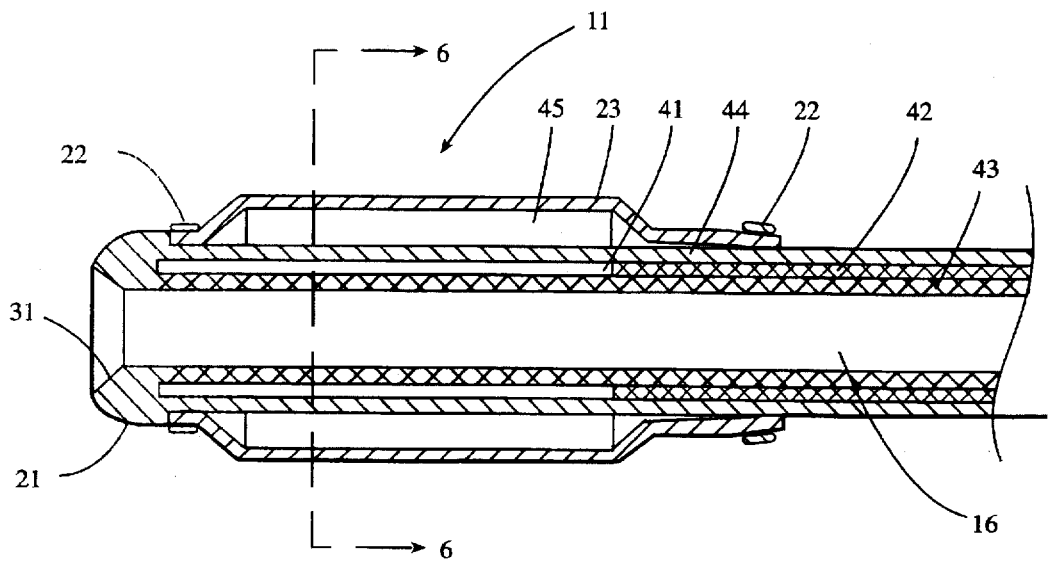
FIG. 4 is a horizontal cross-sectional view of the catheter tip of FIG. 2.

FIG. 4 is a cross-sectional view of the catheter tip shown in FIG. 2. The radiopaque bands 22 are shown on the proximal and distal ends of the balloon 23. The balloon 23 is inflated with an inflation medium (not shown) through a port (not shown in this view). The fiber optic array 42 is contained between the outer sheath 44 and the inner sheath 43. The fiber optics 42 deliver light from a source (not shown) to the diffusing medium 41. All the components are arranged concentrically around the guidewire lumen 16.

Figure 5:
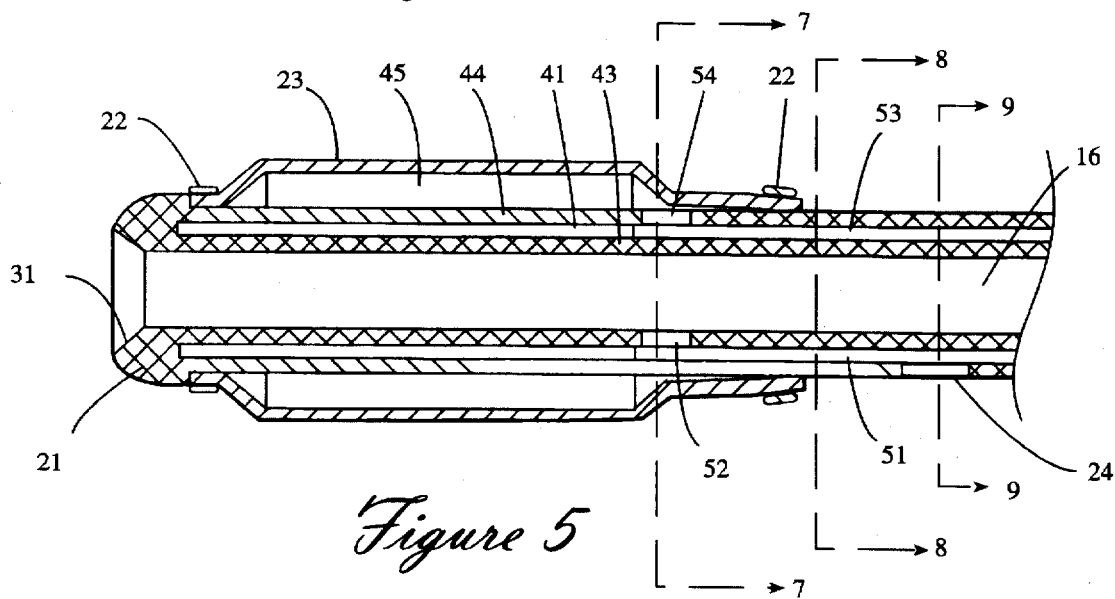
FIG. 5 is the same cross-sectional view as in FIG. 4 rotated 30 degrees.

FIG. 5 shows the same cross-sectional view as in FIG. 4, except rotated 30 degrees. The rotation allows the illustration of the perfusion hole 24, perfusion channel 51, balloon inflation/deflation channel 53, and the balloon inflation/deflation orifice 54. The perfusion hole 24 allows the fluid from the lumen being treated to enter the perfusion channel 51 where it then enters the guidewire lumen 16 via the perfusion port 52. Ultimately the fluid is returned to the lumen distal to the balloon through the introducer cone 31. The balloon inflation/deflation channel 53 is in fluid communication with the inflation/deflation port 14 shown in FIG. 1. The inflation medium 45 is injected through the inflation/deflation port 14, which then travels through the balloon inflation/deflation channel 53 and enters the balloon interior 23 through the balloon inflation/deflation orifice 54 to expand the balloon.

Figure 6:
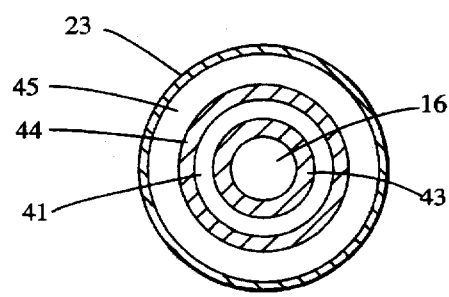
FIG. 6 is a cross-sectional view of the catheter tip of FIG. 4 along section line 6—6.

FIG. 6 shows a cross-sectional view of the catheter tip along section lines indicated in FIG. 4. Centrally located is a guidewire lumen 16. Surrounding the guidewire lumen 16 is the inner sheath 43, the diffusing medium 41, the outer sheath 44, the inflation medium 45 and the balloon 23 concentrically arranged.

Figure 7:
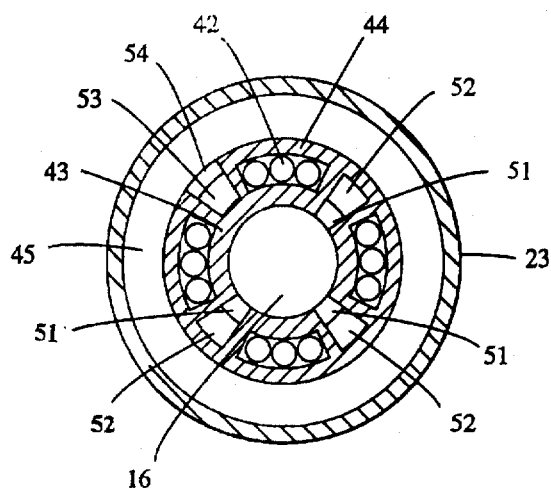
FIG. 7 is a cross-sectional view of a 9-lumen photodynamic angioplasty catheter of FIG. 5 taken along section line 7—7.

FIG. 7 shows a 9 lumen catheter tube. The central lumen is the guidewire lumen 16. Surrounding the guidewire lumen 16 is the inner sheath 43 with 3 cut-outs which represent the 3 perfusion ports 52. The cut-outs allow the perfusion channels 51 to transfer the perfusate to the guidewire lumen 16 through the perfusion ports 52. Concentrically arranged around the guidewire lumen 16 and between the perfusion channels 51 are the fiber optics 42. Around the fibers 42 and the perfusion channels 51 is the outer sheath 44 with a cut-out which allows the inflation medium 45 to exit the balloon inflation/deflation channel 53 and enter the balloon 23 through the balloon inflation/deflation orifice 54.

Figure 8:
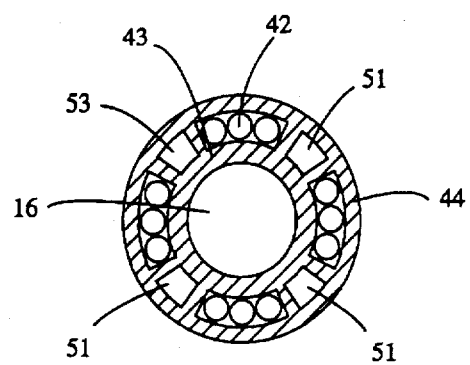
FIG. 8 is a cross-sectional view of the catheter tip of FIG. 5 taken along section line 8—8.

FIG. 8 shows a cross-sectional view of the catheter tip proximal to the balloon 23. The channels are such that the fluids, either inflation medium 45 or the perfusate, are contained within the balloon inflation/deflation channel 53 or the perfusion channel 51. Again the center lumen is the guidewire lumen 16 surrounded by the inner sheath 43 which is surrounded by the three perfusion channels 51, the balloon inflation/deflation channel 53 and the fiber optics 42. The outer-most layer is the outer sheath 44.

Figure 9:
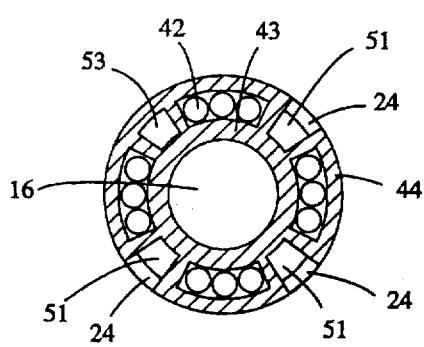
FIG. 9 is the cross-sectional view of the catheter of FIG. 5 taken along section line 9—9.

FIG. 9 shows the three perfusion holes 24 in communication with the three perfusion channels 51, which allows the perfusate to enter the catheter tip 11. The components previously described are shown as indicated. The diameter of the catheter can range from 1 mm to 5 mm, depending upon the application. The balloon diameter can range from slightly larger than 1 mm to 3 cm and larger. The materials used are the typical biocompatible plastics such as polyurethane or high strength polyester. The balloon itself can be made from polyethylene or high strength polyester, both materials being strong and transparent to visible wavelengths of light.

Figure 10:
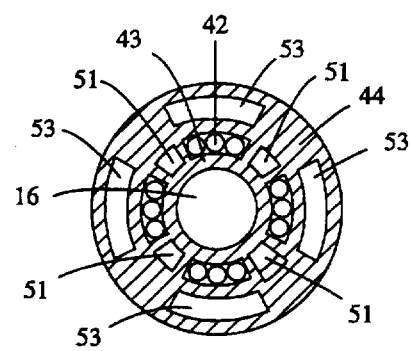
FIG. 10 is a cross-sectional view of a 13 lumen photodynamic angioplasty catheter similar to that shown in FIG. 5 along line 8—8.
Figure 11:
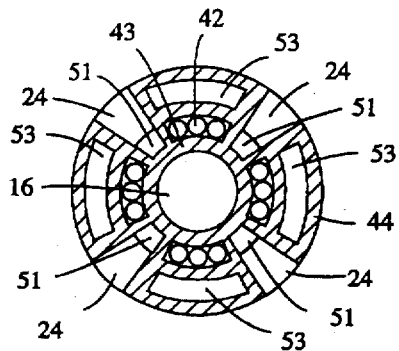
FIG. 11 is a cross-sectional view of the catheter described in FIG. 10 along section line 9—9 of FIG. 5.
Figure 12:
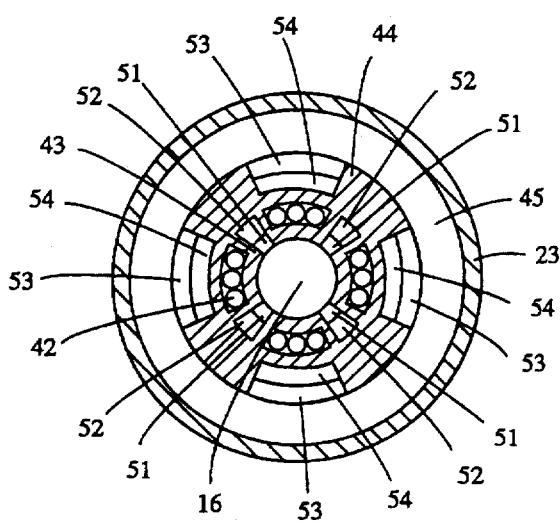
FIG. 12 shows a cross-sectional view of a 13 lumen catheter similar to the 9 lumen catheter of FIG. 5 taken along section line 7—7.

FIGS. 10 through 12 show a 13-lumen embodiment of the balloon perfusion catheter of the present invention. The cross-sectional views in FIGS. 10 through 12 correspond to the respective section lines 7—7 to 9—9 in FIG. 5.

FIG. 10 shows a cross-sectional view of the 13-lumen catheter tip proximal to the balloon 23 taken at section line 8—8 (FIG. 5). The channels are such that the fluids, either inflation medium 45 or the perfusate, are contained within the four balloon inflation/deflation channels 53 or the four perfusion channels 51. Again, the center lumen is the guidewire lumen 16 surrounded by the inner sheath 43 which is surrounded by the 4 perfusion channels 51, the four balloon inflation/deflation channels 53 and the fiber optics 42. The outer-most layer is the outer sheath 44.

FIG. 11, which is a cross-sectional view of the 13-lumen catheter taken at section line 9—9, shows the 4 perfusion holes 24 in communication with the 4 perfusion channels 51, which allows the perfusate to enter the catheter tip 11.

FIG. 12 is a cross-sectional of a 13-lumen catheter taken along section line 7—7 of FIG. 5. The central lumen is the guidewire lumen 16. Surrounding the guidewire lumen 16 is the inner sheath 43 with four cut-outs which represent the four perfusion ports 52. The cut-outs allow the perfusion channels 51 to transfer the perfusate to the guidewire lumen 16 through the perfusion ports 52. Concentrically arranged around the guidewire lumen 16 and between the perfusion channels 51 are the fiber optics 42. Around the fibers 42 and the perfusion channels 51 us the outer sheath 44 with a cut-out which allows the inflation medium 45 to exit the four balloon inflation/deflation channels 53 and enter the balloon 23 through the four balloon inflation/deflation orifices 54.

For applications which require use of this catheter in a blood field, coating the catheter with heparin or a similar anticoagulant would be advisable. Since the blood will be flowing through the device, blood coagulation could become a problem. Heparin coatings are common in angioplasty catheter and should obviate any difficulties with blood coagulation. Retracting the guidewire for vascular applications will increase blood flow through the catheter. The use of an exterior hydromer coating such as hydrogel may also be employed to facilitate the introduction and passage of the catheter through vascular tortuosities.

All the above described advantages provide a photodynamic angioplastic catheter in accordance with the present invention that offers improved performance, greater versatility, increased cost-effectiveness, improved convenience and ease of use as compared to prior art devices of this general nature.

It will be appreciated that, while a preferred embodiment of the invention has been described herein, various modifications will suggest themselves to those skilled in the pertinent arts. For example, variations in the configuration of the invention may be devised to adapt the present invention for use in bodily passages or cavities other than blood vessels. The above-described embodiment for intravascular angioplasty employs a guidewire lumen as a portion of the perfusion channel. The perfusion ports located proximal to the balloon may have a dedicated lumen to conduct fluids from the proximal side of the balloon to the distal side, obviating the need for a guidewire lumen. Or, the guidewire lumen may be used as a perfusion channel to deliver exogenous fluids such as oxygen transporting blood substitutes (i.e., Fluosol®) or air-jetted oxygen for respiratory tract applications, to a point distal to the balloon while the balloon is inflated or even if the balloon is not inflated.

The essential feature of the perfusion catheter of the present invention is that transluminal fluid communication around the inflated balloon is maintained during photoirradiation or an interluminal surface. The specific configuration of the catheter lumens and their relative sizes and numbers may be modified to accommodate increased fluid flow and/or optical components of different sizes. Of course, the catheter according to the teachings herein can be used for high power applications such as tissue welding and hyperthermia. The ability to conduct fluids around the balloon enables the diversion of potentially cooling fluids around the area being treated.

These and other modifications that may suggest themselves to those skilled in the pertinent arts are considered to be within the spirit and scope of the present invention as defined in the claims which follow.

What I claim is:

1. An intravascular balloon catheter operable for administering a dosage of diffuse therapeutic light to uniformly illuminate the inner surface of a cylindrical portion of a blood vessel without interrupting the flow of blood through the blood vessel, said balloon catheter comprising:

(a) a flexible elongate catheter body having a non-invasive proximal portion, a non-shadowing invasive distal portion terminating distally in a tip opening and a central lumen terminating at said tip opening, said catheter body being made from an outer sheath, a portion of which is optically transparent at said invasive distal portion, and an inner sheath disposed coaxially within said outer sheath; said catheter body further having an optically transparent inflatable balloon concentrically overlying said optically transparent portion of said outer sheath and affixed to said outer sheath to form a fluid-tight connection therewith, said balloon comprising an inflatable optically transparent outer shell enclosing an inner chamber;

(b) a cylindrical light diffuser element disposed between said optically transparent portion of said outer sheath and said inner sheath under said balloon, said cylindrical light diffuser element having a proximal end adapted to receive light, said light diffuser element providing means operable for delivering treatment light to uniformly illuminate a circumferential portion of a blood vessel adjacent to and encircling said outer shell of said balloon;

(c) multiple channels located between said inner and outer sheaths, said multiple channels extending from said proximal portion to said cylindrical light diffuser element, each of said channels being separate from each other and parallel to said central lumen, one of said channels being an inflation lumen in fluid communication with said inner chamber of said balloon for conducting the flow of an optically transparent fluid inflation medium therethrough;

(d) an inflation fluid injection port mounted on said exterior surface of said non-invasive portion of said catheter body, said fluid injection port operable for introducing an optically transparent inflation medium into said inflation lumen;

(e) a fiber optic array disposed within another one of said multiple channels, said fiber optic array having a proximal end adapted to receive treatment light from a light source, and a distal end operatively connected to said cylindrical light diffuser element, said fiber optic array operable for conducting treatment light from said proximal end to said diffuser element;

(f) a first opening in said outer sheath of said invasive distal end of said catheter body proximal to said balloon and a second opening in said inner sheath proximal to said diffuser element, said first and second openings being in fluid communication with one of said multiple channels, said second opening further in fluid communication with said central lumen, said openings and said multiple channel forming a perfusion channel providing fluid communication between the exterior of said catheter body and said central lumen operable for continued blood flow through a blood vessel during treatment even though the blood vessel may be occluded by said balloon when said balloon is inflated.

2. A method for performing phototherapy of a diseased target tissue on the interior wall of a blood vessel comprising the steps of:

(a) inserting the invasive distal portion of a balloon perfusion light delivery catheter into the blood vessel, the invasive distal portion having: (i) an axially symmetric cylindrical light diffusing element disposed within a wall of said invasive distal portion of said cathether; said light diffusing element being operable for receiving treatment light from a source of treatment light and directing the treatment light to uniformly illuminate the diseased target tissue, and (ii) an optically transparent inflatable balloon affixed to said invasive distal portion and concentrically overlying the light diffusing element;

(b) advancing the invasive distal portion of the balloon perfusion catheter through the blood vessel until the balloon is adjacent to the diseased target tissue;

(c) inflating the balloon until the transparent wall of the balloon substantially occludes the blood vessel and presses against the diseased target tissue on the interior wall of the blood vessel to displace blood therebetween and prevent blood from entering between the balloon wall and the target tissue on the inner wall of the blood vessel;

(d) presenting a treatment light output source, said treatment light being operable for performing phototherapy of a cylindrical portion of the diseased target tissue, and providing optical connection means for conducting the treatment light from the treatment light output source to the light diffusing element;

(e) perfusing blood in the blood vessel past the inflated balloon through a wall of said invasive distal portion of said catheter while continuously illuminating tissue on the inner wall of the blood vessel adjacent to the balloon and comprising the diseased target tissue until a therapeutically effective dosage of treatment light has been administered to the diseased target tissue.

* * * * *